United States Patent [19]

Janis et al.

[11] Patent Number: 5,126,432

[45] Date of Patent: Jun. 30, 1992

[54] CALCIUM CHANNEL MODULATING SUBSTANCES

[75] Inventors: Ronald A. Janis, Orange; David E Johnson, North Haven, both of Conn.

[73] Assignee: Miles Inc., Elkhart, Ind.

[21] Appl. No.: 157,640

[22] Filed: Feb. 12, 1988

[51] Int. Cl.$^5$ .................... C07K 3/00; C07K 13/00; C07K 15/00; C07K 17/00
[52] U.S. Cl. .................................... 530/350; 530/412
[58] Field of Search ........................................ 530/350

[56] References Cited

PUBLICATIONS

Ferro et al., Chem. Abstracts, 107(13):111693a (1987).

*Primary Examiner*—Johann Richter
*Attorney, Agent, or Firm*—E. Gray, M.G. Boguslaski

[57] ABSTRACT

Endogenous calcium channel modulating substances isolated from mammalian tissue are disclosed. Said substances act on dihydropyridine-sensitive calcium channels to reversibly modulate the activity thereof.

3 Claims, 6 Drawing Sheets

CALCIUM CHANNEL MODULATING SUBSTANCES

BACKGROUND OF THE INVENTION

In recent years, considerable effort has been expended in an attempt to develop new therapeutic agents for the treatment of angina pectoris and associated symptomatology representative of cardiovascular disease. Of such agents, the calcium channel blockers have met with widespread acceptance. Calcium channel antagonists (as they are alternatively referred to) possess diverse chemical structures. These agents possess the ability to block the influx of extracellular calcium during cardiac and vascular smooth muscle depolarization thus leading to a decrease in cytosolic calcium concentration and the concomitant physiological manifestations. Calcium channel agonists are potentially useful in the treatment of heart failure.

Research into the design and synthesis of new chemical entities which can block the calcium channel has progressed largely based on drug screening studies per se in both smooth and cardiac muscle. Such studies have led to speculation concerning the existence of endogenous substances which modulate the activity of the calcium channel and which have therapeutic and diagnostic implications which will be discussed in detail below.

DESCRIPTION OF PERTINENT ART

All publications cited in this document are expressly incorporated herein by reference.

Janis et al (J. Clin. Pharmacol., 23, 266-273, 1983) have reported that small quantities of human and rat serum inhibited the binding of the calcium channel antagonist, nitrendipine, leading to speculation of the existence of one or more endogenous materials which may modify the activity of calcium channels.

S. A. Thayer et al (9th International Congress of Pharmacology Abstracts, 1984) disclose a soluble crude fraction from brain homogenates which is said to perhaps be associated with calcium channel function. This fraction is described as being able to inhibit the specific binding of [$^3$H]nitrendipine to a high affinity binding site; this binding is said to be non-competitive and is modulated by divalent cations. Said fraction is described as having a molecular weight of between 5,000 and 10,000 daltons, is heat labile and is not destroyed by trypsin. It is further reported by Thayer et al that this crude material produces alterations in the contractile response of the guinea pig ileum to carbachol which suggests that the material may modulate transmembrane calcium fluxes.

Additionally, preliminary reports by Hanbauer and Sanna (*Clinical Neuropharmacology*, 9, Supp. 4, 220-222 1986) and Ebersole et al (*Fed. Proc.*, 46, 394, 1987) suggest the presence of some 1,4-dihydropyridine (DHP) inhibiting substance in brain. However, none of the above publications report evidence of any direct effects of said substances on calcium channel current nor do those substances have physical characteristics similar to those of the instant claimed invention.

An abstract of results obtained with the active complex extracted from brain tissue disclosed herein was published in Pharmacologist 29:191 (1987).

SUMMARY OF THE INVENTION

The present invention is directed, in one aspect, to an endogenous calcium channel modulating substance characterized in that the modulating substance is obtained from mammalian brain or pituitary gland tissue by extracting said tissue with a solution of about 1 normal HCl, 1% trifluoroacetic (TFA) acid, 5% formic acid and 1% NaCl. The active complex that elutes from a $C_{18}$ reverse phase column at approximately 26%-33% acetonitrile using gradient elution in 0.1% trifluoroacetic acid has a molecular weight on sodium dodecylsulfate gels of about 18,000 to 20,000 daltons. The active complex elutes from Bio-Sil HT hydroxylapatite between 0.1 M and 0.2 M sodium phosphate (pH 7). On gel filtration with a Waters Protein-Pak 125 column the modulating substance elutes bound to peptides having a molecular weight of approximately 18,000 to about 25,000 daltons forming an active complex. The modulating substance is separated from an about 18,000 dalton peptide by chromatography with about 40% acetonitrile on Bio-Rad Bio-Sil TSK-250 columns and has a molecular weight of less than 1,000 daltons. The modulating substance and active complex inhibit the binding of the tritiated calcium channel antagonist, PN 200-110 (referred to herein as [$^3$H]DHP), to cardiac and brain membranes; the modulating substance inhibits the slowly inactivating $Ca^{2+}$ channel in rat $GH_3$ anterior pituitary cells in a time- and voltage-dependent manner when added to the outside of the cell; and the inhibitory activity is stable to boiling.

In a second aspect, the present invention is directed to an endogenous calcium channel modulating substance characterized in that the modulating substance is obtained from mammalian stomach tissue by extracting said tissue with a solution of about 9% concentrated HCl, 1% trifluoroacetic acid, 5% formic acid and 1% NaCl. The substance elutes bound to a peptide as an active complex having a molecular weight of about 7000 to 10,000 daltons from a Waters μBondapak $C_{18}$ reverse phase analytical Radial-pak column at approximately 47%-50% acetonitrile using gradient elution in 0.1% trifluoroacetic acid. This low molecular weight substance is not retained on a $C_{18}$ column in 0.1% TFA. The substance and the complex inhibits the binding of tritiated calcium channel antagonist, PN 200-110, to cardiac membranes. On gel filtration with a Bio-Rad Bio-Sil TSK-250 column in about 40% acetonitrile, the modulating substance is separated from the complex and has an apparent molecular weight of less than 1000 daltons. The substance reversibly inhibits the slowly-inactivating $Ca^{2+}$ channel in rat $GH_3$ anterior pituitary cells in a time- and voltage-dependent manner when added to the outside of the cell. Its effect on the calcium channel is reversed by hyperpolarization of the cell membrane.

In a third aspect, the present invention is directed to endogenous calcium channel modulating substances characterized in that the modulating substances are obtained from mammalian brain tissue by extracting the lyophilized brain tissue with a solution of hexane. On a Baker Cyano Solid Phase Extraction (SPE) CN column, the modulating substance elutes with carbon tetrachloride. On a Baker Cyano column (4.6×25 mm) equilibrated in 99% hexane/1% tetrahydrofuran (THF), the substance elutes with 9%-13% THF. The substance inhibits the binding of the tritiated calcium channel antagonist PN 200-110 to cardiac membranes and reversibly inhibits the slowly-inactivating $Ca^{2+}$ channel in rat $GH_3$ anterior pituitary cells when added to the outside of the cell.

In a fourth aspect, the present invention is directed toward endogenous calcium channel modulating substances obtained from hot methanol extracts of bovine brain (starting material obtained from Sigma Chemical Co., Cat. No. B-1877). These active materials were obtained from hexane extraction of the above starting material and elution of the active fraction from Baker SPE CN columns with carbon tetrachloride and methanol. The active materials inhibited [$^3$H]DHP binding to cardiac membranes. One of the active substances eluting with chloroform was found to inhibit nitrendipine binding to antibodies to nitrendipine and to produce an apparent stimulation of [$^3$H]DHP binding to cardiac membranes.

In a fifth aspect, the present invention is directed to an endogenous calcium channel modulating substance characterized in that said substance is obtained from mammalian brain tissue by extracting said lyophilized tissue with a solution of hexane. On a Baker Cyano Solid Phase Extraction (SPE) column said substance elutes with chloroform. This fraction produces an apparent stimulation of DHP binding to cardiac membranes. It also produces an increase or decrease in slowly-inactivating calcium channel current in $GH_3$ cells.

The general method of isolation from mammalian tissues comprises the steps of:

a) homogenizing said mammalian tissue in an acid or salt solution capable of solubilizing a modulating substance or an active complex of the substance;

b) subjecting the homogenate to $C_{18}$ reverse phase chromatography capable of separating fractions eluting at about 30%–50% acetonitrile that inhibit [$^3$H]DHP binding to cardiac membranes;

c) subjecting the separated fractions to chromatography including a chromatography with greater than 35% acetonitrile on a gel filtration column capable of providing equivalent separation to a Bio-Rad Bio-Sil TSK 250 column; and d) isolating from said column said endogenous calcium channel modulating substance.

DETAILED DESCRIPTION OF THE INVENTION

Figure 1:
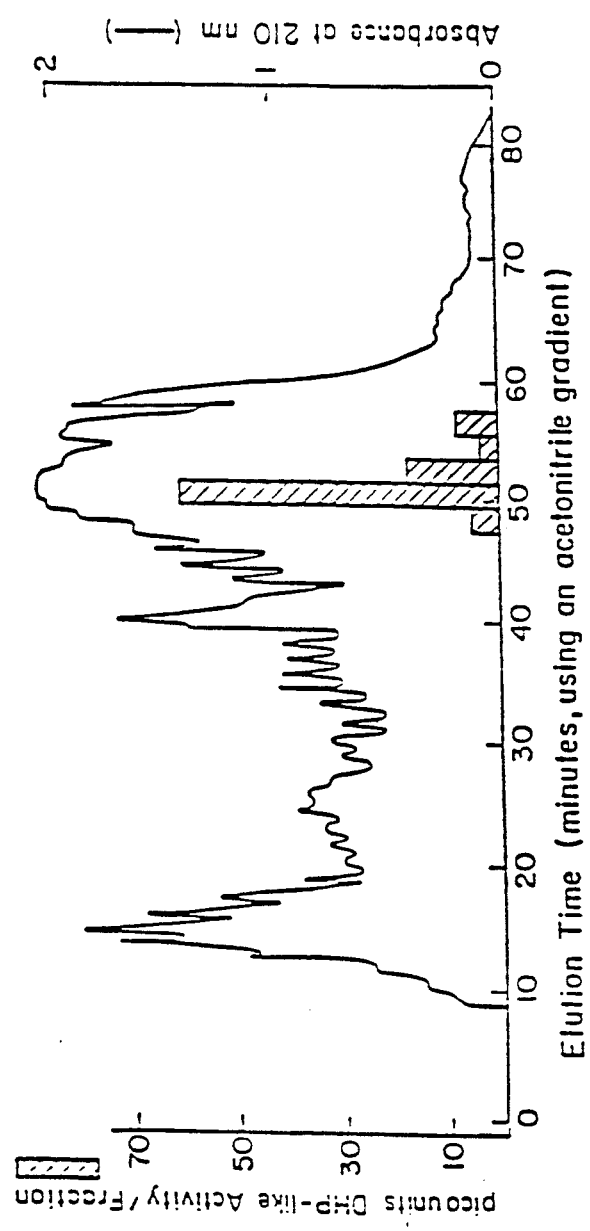
FIG. 1 represents the location of active fractions (hatched area) isolated from calf brain (Example 1).

The endogenous substances of the present invention may be isolated from mammalian tissues containing the substances by techniques which have general applicability to the extraction and isolation of endogenous substances from mammalian tissues or fluids. In particular, the calcium channel modulating substances of the present invention are obtained from mammalian tissue or fluid by acid, hexane or methanol extraction. This material is then chromatographed on a preparative reverse-phase column using an acetonitrile/trifluoroacetic acid solution as the eluent. The percent acetonitrile at which the complex elutes for $C_{18}$ reverse phase HPLC columns will depend on many factors, such as how new the column is, what it was used for previously, which are well known to those skilled in the art of natural product purification. However, by using [$^3$H]DHP binding to assay a part of each fraction, the important peptide complex can be located.

In the case of the hexane and methanol extractable substances, Baker SPE CN columns may be used for isolation. The various fractions are then collected and dried and assessed for activity as, for example, by measuring the inhibition of [$^3$H]PN 200–110 (see infra) to rat heart membranes by the method of Janis et al, supra. The endogenous calcium channel modulating substances of the present invention are preferably, though not necessarily exclusively, isolated from mammalian brain and stomach tissue. The endogenous substance is isolated from the tissue as substantially purified material which did not exist in such form in the tissue from which it was obtained.

In two cases the fraction from the $C_{18}$ column was found to consist of a low molecular weight organic substance of less than 1000 daltons bound to a peptide having a molecular weight greater than 5000 but less than 30000 daltons and was found to inhibit [$^3$H]DHP binding to cardiac membranes. For an active preparation obtained from brain tissue, the active complex has a molecular weight between 18,000 to 20,000 daltons. For an active preparation obtained from stomach, the active complex has a molecular weight between 7000 and 10,000 daltons. In general it was found that both the low molecular weight portion and the complex, inhibit 1,4-dihydropyridine binding to cardiac membranes and inhibit the slowly inactivating calcium channel of $GH_3$ cells when placed inside the cell, but only the low molecular weight substances inhibit the slowly inactivating calcium channel in rat $GH_3$ anterior pituitary cells in a time- and voltage-dependent manner when added to the outside of the cells.

The fractions found to be active by [$^3$H]DHP binding are then subjected to size exclusion chromatography by gel filtration on a column having equivalent separation to a Bio-Rad Bio-Sil TSK 250 column in greater than 35% acetonitrile, preferably about 40%. The fractions are again analyzed for inhibition of [$^3$H]DHP binding to cardiac membranes to find low molecular weight fractions which inhibit [$^3$H]DHP binding and calcium channel current.

In addition, an active preparation capable of exhibiting calcium channel modulating properties has been found after direct extraction from brain with a nonpolar organic solvent such as hexane. The active preparation has been separated into several active fractions by extraction from a cyanopropyl column of the active preparation with organic solvents of increasing polarity, i.e. carbon tetrachloride, chloroform, methanol. An active substance found by extraction with chloroform exhibited stimulator activity as detected by ligand binding and increases calcium currents in an electrophysiological assay. This substance or substances could be useful as an agonist.

The active substance that was extracted with carbon tetrachloride inhibited DHP binding to cardiac calcium channels and inhibited slowly inactivating calcium channels of $GH_3$ cells.

An active preparation capable of exhibiting calcium channel modulating properties has also been found after direct extraction from brain with a polar organic solvent such as methanol.

This discovery that basic peptides inhibit [$^3$H]DHP binding may indicate that certain basic peptides modulate $Ca^{2+}$ channels The less than 1000 dalton fractions from the gel filtration columns (40% acetonitrile) not only inhibited [$^3$H]DHP binding, but more importantly, specifically inhibited slowly inactivating $Ca^{2+}$ channels when added to the outside of $GH_3$ cells.

As noted previously, these endogenous substances act on calcium channels to modulate the activity thereof. Accordingly, said substances find utility in applications where the calcium channel antagonists or agonists in general are currently being used. These applications include various cardiovascular indications such as angina pectoris (vasospastic and chronic stable), atrial flutter and fibrillation, cardioplegia, hypertension, myocardial ischemia and failure, peripheral vascular disease and the like; cerebral insufficiency; migraine; subarachnoid hemorrhage; asthma; esophageal motor disorders, among others. Of course, the endogenous substances may also find therapeutic efficacy in other disease states. As future uses for calcium channel antagonists or agonists are elucidated, the endogenous substances of the present invention may also find application therein. It is expected that the low molecular weight substances will be useful for drug design, diagnosis of diseases, and development of drugs that effect the synthesis, metabolism or storage of the endogenous modulating substances.

The following examples are provided as a means of illustrating the present invention and are not to be construed as a limitation thereon.

EXAMPLE 1

Isolation and Analysis of Endogenous Substance From Calf Brain a) Extraction

Fifty calf brains from a local slaughterhouse (or, alternatively, 1 kilogram of lyophilized calf brain available from Burlington Bio-Medical Corp., New York) were homogenized with a PT45 probe (Brinkman Instruments, New York) for 2 minutes at setting 6 in 21 liters (L) of the following extraction solution (Quirion et al, *Peptides* 5:967-973, 1984): 9% HCl, 5% formic acid, 1% trifluoroacetic (TFA) acid, and 1% NaCl. The homogenate was centrifuged for 45 minutes at 16,000 ×g resulting in 19 L of material which was extracted 2 times with petroleum ether at a ratio of 2:1 (ether:sample). The aqueous phase from this extraction (13 L) was adjusted to pH 2 with NaOH and subjected to ultrafiltration with a Pellicon (Millipore) apparatus using a 30,000 molecular weight exclusion filter. The fraction of less than 30,000 daltons was chromatographed as follows.

b) Chromatography

The fraction of less than 30,000 daltons was subjected to reverse-phase chromatography on a Waters $C_{18}$ reverse phase preparative column (5.7×30 centimeters) and run in a Waters Prep 500A HPLC system. The fraction was loaded onto the column (which had been previously equilibrated in 0.1% TFA) through the pump at a rate of 100 milliliters per minute (mL/min). The column was washed with 0.1% TFA to remove salts and other non-binding material and then eluted with a 90 minute acetonitrile gradient (0%-70%) in 0.1% TFA at 0.62% acetonitrile per minute at 150 mL/min. Forty-six 300 milliliter (mL) fractions were collected and 10 mL aliquots of each were dried in a Speed Vac (Savant Instruments, New York). The activity eluted from the $C_{18}$ column (as subsequently determined in the ligand binding assay and confirmed by electrophysiology, infra) at approximately 26%-33% acetonitrile and is graphically represented as the hatched area in FIG. 1.

Hydroxylapatite (Bio Gel HT commercially available from Bio-Rad, Inc.) was washed and equilibrated to pH 7 in 0.01 molar (M) sodium phosphate. 3-5 milligrams (mg) of the active brain fractions obtained from the reverse phase chromatography, above, were dissolved in the above sodium phosphate buffer and adjusted to pH 7 with NaOH. Any precipitate which resulted was removed by centrifugation and the resultant supernatant (1 mL representing 3-5 mg protein) was applied to the hydroxylapatite column. Fractionation on said column showed a peak of activity (as subsequently determined) which eluted between 0.1 and 0.2 M sodium phosphate (pH 7). The activity appeared to be associated with the approximately 18,000 to 20,000 dalton proteins as determined on sodium dodecylsulfate gels.

This 18,000 to 20,000 dalton material eluted from a Waters SP-5PW cation-exchange column between 0.4 and 0.55 M NaCl using a NaCl gradient from 0.01 M to 0.8 M in 75 minutes which contained 10% acetonitrile and 20 millimolar (mM) Tris at pH 7.5. Chromatography of said material (obtained from the reverse phase chromatography) on a Waters DEAE-5PW anion-exchange column previously equilibrated in 0.02 M NaCl, 0.02 M Tris pH 8, showed that the activity did not bind to the column when the sample was injected in a solution of the same composition. Chromatography of the active brain fractions (obtained from the reverse phase chromatography) on a Waters Protein-Pak 125 gel filtration column showed that the active substance(s) in the DHP binding assay eluted in a volume range equivalent to 18,000 to 25,000 daltons and to less than 1,000 daltons when using a mobile phase containing 40% acetonitrile, 0.1% TFA. The purified mixture of 18,000 and 20,000 dalton proteins from the SP-5PW cation-exchange column was further purified to apparent homogeneity on a Waters μBondapak $C_{18}$ (8 mm×10 cm) Radial-Pak cartridge. Said proteins eluted at 32% and 33% acetonitrile respectively, when eluted with the following gradient: 0%-26.4% acetonitrile in 20 minutes and then 26.4% to 40% acetonitrile in 27 minutes. The gradient contained 0.1% TFA throughout.

Although the fractions containing the large peptides inhibited DHP binding, and therefore may modulate calcium channel function in the intact cell, these large peptides were not active when tested for their effect on calcium channel current. The low molecular weight fraction was active on calcium channels of GH3 cells.

The active fractions from the above preparative HPLC column were also purified on a Bio-Rad Bio-Sil TSK-250 HPLC column (7.5×300 mm) using a mobile phase of 0.1% TFA/40% acetonitrile and run at a flow rate of 0.5 mL/min. The active fractions (as determined by ligand binding and anti-nitrendipine antibodies) eluted in the range of 9.5 to 12.5 mL. The estimated molecular weight of the active substance capable of modulating calcium channel activity was less than 1,000 daltons.

The active fraction from the TSK-250 column was found to inhibit DHP binding to cardiac membranes. The recovery of this step was estimated to be 0.3 to 0.4 picounits/mg (by weight) of protein from the preparative HPLC column. The active fractions from the TSK-250 column were further purified on a Baker Cyano HPLC column equilibrated in 9% tetrahydrofuran/91% hexane. The column was eluted with a linear gradient of 1% tetrahydrofuran/min in hexane. The active fractions eluted between 19% and 22% tetrahydrofuran determined by ligand binding. This fraction was also found to inhibit slowly inactivating calcium channel current in GH cells.

c) Ligand binding assay

Preparation of microsomes and ligand binding was carried out essentially as described previously by Janis et al, J. Clin. Pharmacol., supra. Frozen rat hearts (Pel-Freeze) were thawed in 50 mM HEPES buffer (i.e., N-2-hydroxyethylpiperazine-N'-2-ethanesulfonic acid, free acid), pH 7.0, and the atria removed. 5 grams (g) of ventricular myocardium were minced with scissors and homogenized in 50 mL HEPES buffer with a Brinkman Polytron PT20 probe at setting 7 for 10 seconds. This was repeated 2 times with a 10 second cooling on ice between each homogenization. The homogenate was centrifuged at 5,000 ×g for 10 minutes at 4° Centigrade (C). The supernatant fraction was removed and centrifuged at 48,000 ×g for 30 minutes. The resultant microsomal pellet was resuspended in buffer and subsequently used in the assay as described below. Protein was determined by the method of Bradford (Anal. Biochem. 72:248-253, 1976) using bovine serum albumin as a standard.

The activity of the fractions isolated by chromatography was defined against a standard curve for competition between the dihydropyridine calcium channel antagonist, nimodipine, and the calcium channel antagonist, isopropyl 4-(2,1,3-benzoxadiazol-4-yl)-1,4-dihydro-2,6-dimethyl-pyridine-3,5-dicarboxylic acid 1-methyl ester (known as PN 200-110 and referred to hereafter as [$^3$H]DHP). The standard curve was derived from data gained by incubating nimodipine and $2 \times 10^{-10}$ M [$^3$H]DHP and microsomal protein per 0.25 ml of assay in 50 mM HEPES buffer (pH 7.0) at 25° C. for 45 minutes and 37° C. for 30 minutes. A cocktail of protease inhibitors ($1 \times 10^{-6}$M aprotinin, $5 \times 10^5$M benzamidine and $5 \times 10^{-5}$M leupeptin) was used but did not inhibit control binding. The cocktail of protease inhibitors is used to prevent breakdown of the isolated fractions during the assay by proteases which may be present in the membranes or fractions themselves and to exclude the possibility that proteases sensitive to these inhibitors contributed to the activity of the fraction. Following incubation, the bound drug was separated from the free by rapid filtration through Whatman GF/B filters using a Brandel Harvester, followed by two consecutive 1 mL buffer washes at 22° C. The filters were placed in scintillation vials with 5 mL of liquid scintillation fluid. Samples were counted in a Beckman LS 1800 liquid scintillation counter at an efficiency of approximately 55%. Nonspecific binding was defined as the amount of radioligand (i.e., [$^3$H]DHP) bound in the presence of nimodipine, which was 10% of total binding.

The fractions isolated from brain were evaluated in the ligand binding assay substantially as described above. Fractions were dissolved in 50 mM HEPES (pH 7.0) and protein concentration was determined by either visible or UV absorption. The pH was carefully monitored and maintained at 7.0 by the addition of 1 M HEPES. All fractions were centrifuged and the supernatants assayed. Binding experiments were performed under sodium vapor light.

d) Results

Fractions eluting from the reverse phase column in the approximately 26%-33% acetonitrile range (as described in Example 1b, above and depicted in FIG. 1) showed activity in the ligand binding assay. The combined activity represented 95 picounits (pU) of total activity, where one pU of activity is defined as being equivalent to the amount of inhibition caused by one picomole of nimodipine which gave equivalent results. The active fractions contained up to 2.5 pU/mg protein from the first chromatographic step. All activity was reversed with the addition of 10 mM $Ca^{2+}$ or by dilution in the presence of 200 mM KCl, meaning that the active fractions acted reversibly and therefore did not represent an enzymatic reaction.

In order to further determine the specificity of action of a particular fraction (i.e., to insure that the fraction was acting competitively on the dihydropyridine receptor and not simply depleting the free ligand), a determination of the amount of free ligand was done by dialysis as follows.

A 12 millimeter (mm) segment of Spectra-por 7 dialysis tubing (0.46 mL/cm) was washed thoroughly with water to remove EDTA and other chemicals. The molecular weight cut-off of this tubing was 1,000. Dialysis was performed in 16 mm glass tubes placed in a shaker incubator at 25° C. overnight. The volume inside the bag (made from closing the tubing by tying it) was 2.5 mL; the outside volume was 10 mL of 50 mM HEPES buffer, pH 7.0. Experiments were done with the [$^3$H]DHP present both inside and outside the bag. The concentration of the [$^3$H]DHP ligand used was always 0.2 nM. A control using 5 mg bovine serum albumin (BSA) inside the bag was carried out. BSA is known to bind [$^3$H]DHP ligand hydrophobically (which is evident because of the increased counts per minute (cpm) associated with BSA inside rather than outside the bag). The brain fractions tested were also 5 mg by weight. Dialysis was carried out in the presence of the cocktail of protease inhibitors described supra present both inside and outside the bag. The experiment was terminated by taking representative aliquots from inside and outside the bag (in triplicate). The cpm were then adjusted for total volume. No [$^3$H]DHP ligand was bound to the fractions tested, demonstrating that the inhibitory activity in the ligand binding assay was not due to a decrease in the free [$^3$H]DHP concentration.

Figure 2:
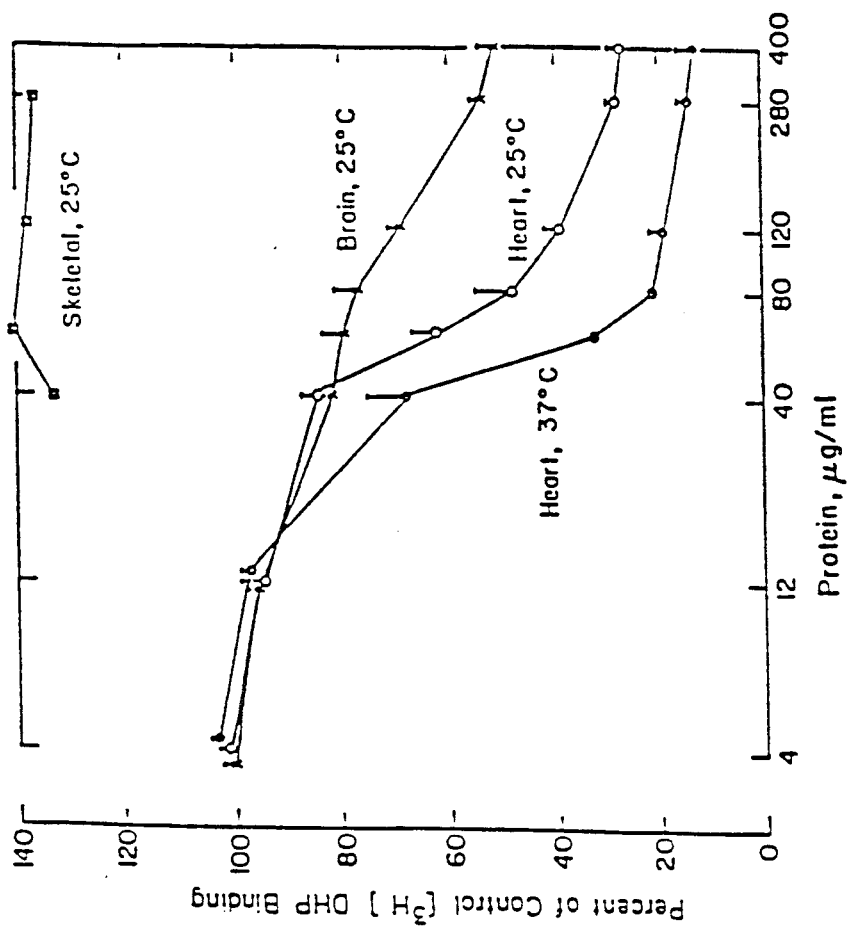
FIG. 2 represents the effect of various amounts of the active complex formed by the protein-endogenous calcium channel modulating substance of Example 1 on the binding of [$^3$H]1,4-dihydropyridine to membranes from skeletal and cardiac muscle and brain.

In further analyses, this endogenous calcium channel modulating substance maintained its inhibitory activity on dihydropyridine receptors when boiled for 30 minutes. This activity was reversed by the presence of 10 mM Ca$^{2+}$, demonstrating reversibility of action. Further, after said substance was heated at 270° C. for 3 hours (in order to ash it), activity was lost further indicating that the substance is organic in nature rather than inorganic (a control of 0.8 M NaCl maintained activity upon ashing). The effect of the endogenous calcium channel modulating substance varied on brain, heart and skeletal muscle membranes (FIG. 2). The substance caused more inhibition in heart than brain membranes and showed stimulation in skeletal muscle membranes. This observed differential activity was further evidence of a specific interaction with the dihydropyridine binding site rather than the non-specific reduction of free ligand concentration.

The low molecular weight (less than 1,000 dalton) fraction was likewise shown to inhibit DHP binding to cardiac membranes. It was also found to inhibit slowly inactivating calcium channel current when added to the outside of GH$_3$ cells, as described in the next section. It was also found to inhibit the binding of tritiated 1,4-dihydropyridine, [H$^3$]nitrendipine, to antibodies to nitrendipine. (The antibodies were prepared and cross-reactivity determined as described by Campbell et al., Proc. Natl. Acad. Sci. USA 83:2792-2796, 1986).

The activity (as measured by inhibition of DHP binding to cardiac membranes) of the low molecular weight fraction was found to elute from a Baker Cyano HPLC column (4.6×250mm) between 19 and 22% tetrahydrofuran.

e) Electrophysiology

In order to further demonstrate that the endogenous calcium channel modulating substance of the present invention inhibits the Ca$^{2+}$ channel, the following study was undertaken (as described by Cohen and McCarthy, J. Physiol., 387:195-225, 1987).

- A 150 mg sample of the calcium channel modulating substance of the present invention was dissolved in 37 mL of 0.05% TFA and 37 mL of methanol. This mixture was shaken together with 150 mL of chloroform in a glass separatory funnel for 10 minutes and then allowed to stand for 1 hour to achieve separation. The upper aqueous phase was collected and freeze-dried. The dried fraction was dissolved in 160 mL of 50 mM HEPES; ultrafiltrated through a 5,000 dalton filter in an Amicon cell and then washed with 2 more washes of 160 mL each of 150 mM HEPES. The retentate yielded 10 pU/mg protein activity and was used for electrophysiology as described below. The fraction was passed through a 5,000 dalton filter in an Amicon cell to remove low molecular weight substances. The retentate retained 90% of the inhibitory activity showing dose-dependent inhibition up to 100 μg protein. Since the majority of the activity was over 5,000 daltons, this step removed any interfering substances and salts under approximately 5,000 daltons.

Rat anterior pituitary (GH3) cells were bathed in Tyrode's solution containing NaCl (150 mM), KCl (4.0 mM), CaCl$_2$ (9.0 mM), MgCl$_2$ (0.5 mM), dextrose (5 mM) and HEPES (10 mM, pH 7.5). The tip of a patch electrode was filled with a solution containing CsCl (108 mM), tetrabutylammonium chloride (10 mM), BAPTA, i.e., 1,2-bis-(2-aminophenoxy)ethane-N,N,N',N'-tetraacetic acid (11 mM), CaCl$_2$ (0.9 mM), MgCl$_2$ (6 mM), adenosine triphosphate (5 mM) and HEPES (20 mM, pH 7.2). This solution is designed to eliminate all potassium channel currents and to slow rundown of the calcium channel currents. After the initial filling of the tip, the patch electrode was back-filled with the above-described solution plus the dissolved endogenous calcium channel modulating substance at a concentration of 0.5 mg/mL. The patch electrode was then mounted under positive pressure to allow both mixing and diffusion of drug into the tip. A high resistance seal was made to the cell by applying negative pressure and subsequently, the membrane beneath the electrode was disrupted by an increase in negative pressure. Recordings of inward calcium channel currents were performed in a bath solution of tetraethylammonium chloride (117 mM), BaCl$_2$ (20 mM), MgCl$_2$ (0.5 mM), tetrodotoxin ($2 \times 10^{-4}$ mM), dextrose (5 mM), sucrose (32 mM) and HEPES (10 mM, pH 7.5).

Time and voltage-dependent block of the slowly inactivating calcium channels by intracellular addition of the endogenous substance of the present invention was obtained in four experiments using three separate fractions. It is known that GH3 rat anterior pituitary cells exhibit little or no inactivation for potentials more negative than −20 millivolts (mV). Over this range, where in control studies there is no inactivation, the endogenous calcium channel modulating substance produced potent time and voltage-dependent block of the dihydropyridine-sensitive calcium channels. The onset of block at variable prepulse durations to more depolarized potentials produced potent calcium channel block. It was also shown that the substance has no effect on the voltage-dependence of activation or inactivation of the transient calcium channels which are believed to be available for opening in the steady state. These results are graphically represented in FIG. 3.

Figure 3:
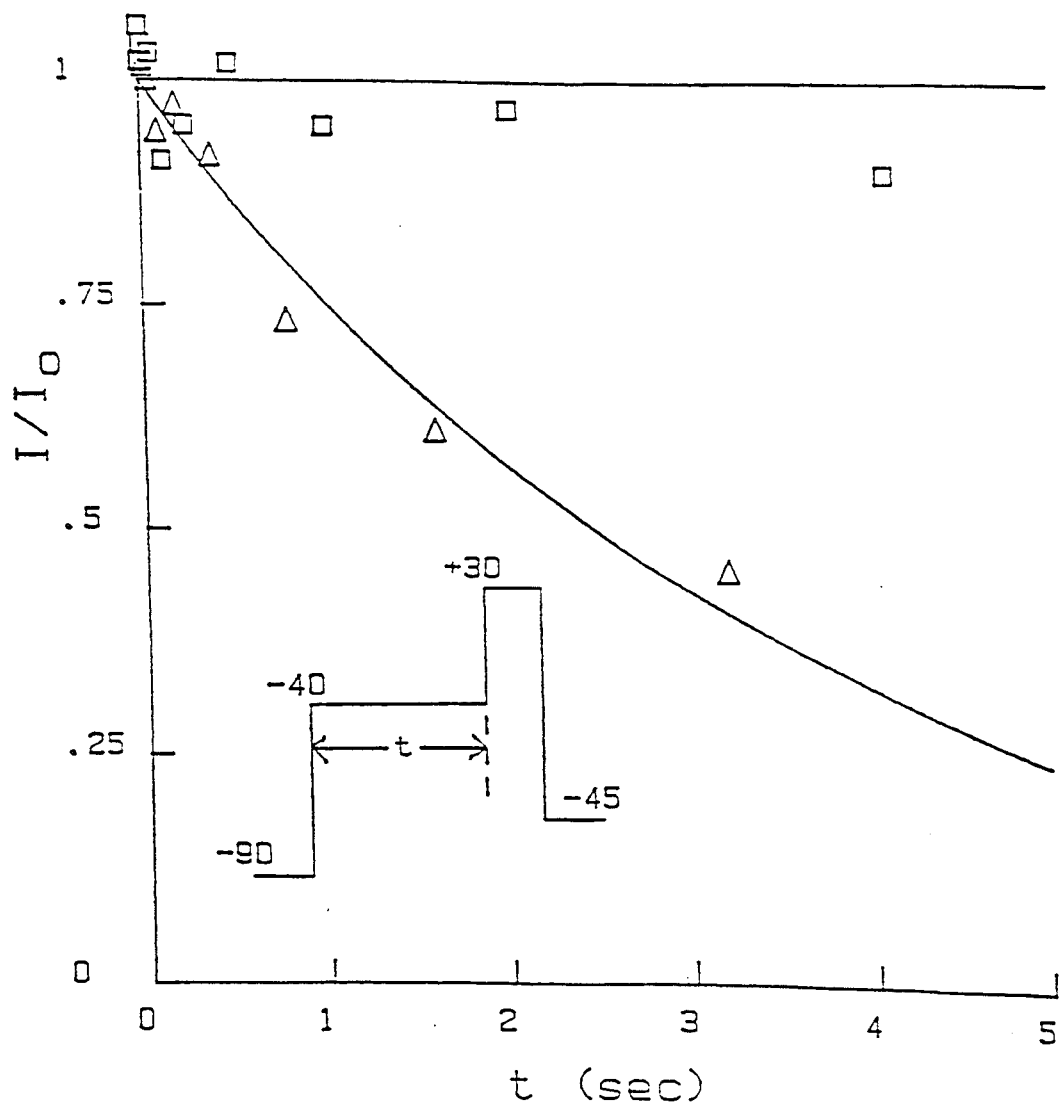
FIG. 3 graphically represents the rate of onset of calcium channel block by the endogenous calcium modulating substance of Example 1.

FIG. 3 shows the rate of onset of calcium channel block by the endogenous substance of the present invention. The same results were obtained when the low molecular weight fraction (obtained from the fraction used in the experiment) was added to the outside of the cells. The time course of block of the slowly-inactivating channels was determined by tail current analysis as described in Matteson and Armstrong (J. Gen. Physiol. 87:161-182, 1986) and Cohen and McCarthy (J. Physiol., 387:195-225, 1987). A protocol was used which takes advantage of the fact that GH$_3$ cells show little inactivation of inward calcium channel current during prolonged test pulses. For each data point, the membrane potential was held at −90 mV and then stepped to the prepulse potential ($V_p = -40$ mV) for a variable duration prepulse (t). Then a 10 millisecond (ms) test pulse to +30 mV produced maximal activation of the slowly-inactivating Ca channels and tail currents were measured upon repolarization ($V_r = -45$ mV) as shown in the inset of FIG. 3. During the control prepulses (open squares), the fast component of tail current corresponding to the slowly-inactivating channels showed little or no inactivation. The data are fit as a normalized mean of 12 points (104.5 picoamps, pA). With increasing prepulse duration, the endogenous calcium channel modulating substance was added to the pipette (open triangles) and produced time- and voltage-dependent block of the calcium channel. The 8 data points found are fit to the equation:

$$I = (I_o - I_\infty) \exp(-t/\tau\text{onset}) + I_\infty. \text{ For } V_p = -40 \text{ mV}, I_o = 143.17 \ pA. \ \tau\text{onset} = 3.56 \text{ sec.}$$

The values were normalized by taking the ratio of the fast tail current amplitudes fit by a single exponential (I) to the value obtained by a curve fitting these data points using a non-linear test squares analysis (Colquhoun, Lectures on Biostatistics, Oxford University Press, London) and extrapolating back to time zero ($I_o$). These normalized values ($I/I_o$) were plotted as the ordinate. The cycle length was ten seconds. The potent time and voltage-dependent, reversible block of the calcium channels demonstrate that the fraction containing the less than 1,000 and 18,000 to 20,000 dalton substances block calcium channels and inhibit dihydropyridine binding. The lack of effect on another type of calcium channel in these cells shows specificity of action for slowly-inactivating calcium channels.

This endogenous calcium channel modulating fraction is described as containing material having a molecular weight of 18,000 to 20,000, and also a material having a molecular weight of less than 1,000 dalton.

The low molecular weight substance that inhibits DHP binding was isolated from the active fraction (31%-33% acetonitrile) obtained from the preparative column procedure described in Example 1b, supra. When this fraction was chromatographed on either a Waters Protein Pak-125 or a TSK-250 gel filtration column using 40% acetonitrile in 0.1% TFA as the mobile phase, the activity (as determined in ligand binding assays described in Example 1c) eluted in a volume less than 8-lipoprotein fragment (amino acids 61-63) having a molecular weight of 443. This activity of this described low molecular weight substance (less than 1,000 daltons) from brain was not completely reversed by 10 mM $Ca^{2+}$ or 4 μM EDTA; it was stable to boiling; and it cross-reacted with antibodies to nitrendipine (the antibodies prepared, and cross-reactivity determined as described by Campbell et al, *Proc. Natl. Acad. Sci. USA* 83:2792–2796, 1986). The latter result, coupled with the inhibition of dihydropyridine binding strongly suggests that this low molecular weight substance is an endogenous dihydropyridine-like substance.

Separation of the large peptides from the less than 1,000 dalton material resulted in the demonstration that the latter produced the same results on calcium channel current as the mixture. The inhibitory effect of the large peptide alone on DHP binding suggests that it acts on calcium channels. The lack of effect of this peptide on calcium current in GH$_3$ cells indicates that its effect on calcium channels is fundamentally different from that of the low molecular weight material. The latter is active from outside the cell suggesting that it could be particularly useful for its effects on calcium channels when used therapeutically, or for the design of new drugs or diagnostic agents based on its structure.

EXAMPLE 2

Isolation of Endogenous Substance From Sheep Pituitary a) Extraction

Lyophilized sheep pituitary (100 g) was obtained from Burlington Bio-Medical Corp., New York. The sheep pituitary was homogenized in 1 L of acid extraction solution (i.e., 1 M HCl, 5% formic acid, 1% TFA and 0.5% NaCl) using a polytron PT20 probe in batches of 500 mL each. The homogenate was centrifuged at 16,000 ×g for 75 minutes. The supernatant was filtered through 4 layers of cheesecloth and the filtrate extracted 2 times with petroleum ether (2:1, ether:sample) to remove lipids. The aqueous phase from the extractions were combined (about 600 mL) and then diluted to 1 L with the acid extraction solution and then filtered through a 30,000 dalton cut-off limit Minitan ultrafiltration apparatus (Millipore). The fraction of less than 30,000 daltons (about 860 mL having a protein concentration of 1 mg/mL) was then chromatographed as described below.

b) Chromatography

The fraction of Example 2a was subjected to reverse-phase chromatography utilizing the same methodology as described in Example 1b. The column was eluted with a 70 minute linear gradient of from 0%-80% acetonitrile in 0.1% TFA. Forty-six 200 mL fractions were collected and 10 mL aliquots of each were dried in a Speed Vac (Savant Instruments, New York). The fractions numbered 34-38 which showed the highest activity were pooled (representing a total volume of 340 mL) and lyophilized or were diluted out with weak buffer and reloaded onto a subsequent reverse phase column for repurification. The fractions were assayed for inhibition of dihydropyridine binding to rat heart membranes as follows.

c) Ligand binding assay

The ligand binding assay described in Example 1c was repeated with the endogenous fractions isolated by chromatography in Example 2b.

d) Results

Activity was observed in the 30%-40% acetonitrile range. This activity was maintained in the presence of 4 μM EDTA. Approximately 50% of the inhibitory activity of the fractions was lost in the presence of 100 μM $Ca^{2+}$. A time course of 45 and 90 minutes did not increase the percent inhibition of any fractions. A 5,000 dalton retentate (prepared as described in Example 1) showed a dose-dependent inhibition up to 100 μg protein. The endogenous substance showed tissue selectivity with brain, heart and skeletal muscle membranes.

Cation exchange chromatography on a Waters SP-5PW column produced a peak of inhibitory activity at 0.4 M ammonium acetate when eluted with a 0.01 to 1.0 M 60 minute gradient at pH 5.5. When chromatographed on a Waters DEAE-5PW anion exchange column using a 60 minute gradient of 0.01 to 0.5 M NaCl (pH 8), the inhibitory activity eluted near the void volume and stimulatory activity eluted at 0.3 M NaCl. These results suggest that at least some of the activity shown by the endogenous substance isolated from the pituitary is due to the same substance as that isolated from brain.

EXAMPLE 3

Isolation and Analysis of Endogenous Substance From Lamb Abomasum a) Extraction

Three hundred grams of lyophilized lamb abomasum (available from Burlington Bio-Medical Corp., New York) were homogenized with a PT45 probe (Brinkman Instruments, New York) for 2 minutes at setting 6 in 6 liters (L) of the following extraction solution (Quirion et al, Peptides 5:967-973, 1984): 9% HCl, 5% formic acid, 1% trifluoroacetic (TFA) acid, and 1% NaCl. The homogenate was centrifuged for 45 minutes at 16,000 ×g resulting in 5 L of material which was extracted 1 time with petroleum ether at a ratio of 2:1 (ether:sample). The aqueous phase from this extraction (4.8 L) was adjusted to pH 2 with NaOH and subjected to ultrafiltration with a Pellicon (Millipore) apparatus using a 30,000 molecular weight exclusion filter. The fraction of less than 30,000 daltons was chromatographed as follows.

b) Chromatography

The fraction of less than 30,000 daltons was subjected to reverse-phase chromatography on a Waters $C_{18}$ reverse phase preparative column (2.5×30 centimeters) and run in a Waters Prep 500A HPLC system. The fraction was loaded onto the column (which had been previously equilibrated in 0.1% TFA) through the pump at a rate of 100 milliliters per minute (mL/min). The column was washed with 0.1% TFA to remove salts and other non-binding material and then eluted with a 90 minute acetonitrile gradient (0%–70%) in 0.1% TFA at at 100 mL/min. Fifty 200 milliliter (mL) fractions were collected and 5 mL aliquots of each were dried in a Speed Vac (Savant Instruments, New York). The activity eluted from the $C_{18}$ column (as subsequently determined in the ligand binding assay and confirmed by electrophysiology, infra) at approximately 43%–48% acetonitrile.

The active fractions obtained from the preparative reverse phase chromatography were further purified on a Waters μBondapak $C_{18}$ analytical reverse phase Radial-pak (8 mm×10 cm). The active component eluted from the column at 47% acetonitrile in the following gradient in 0.1% TFA: 0%–40% in 32 minutes, 40%–70% in 40 minutes.

The highly purified activity from the analytical reverse phase column was chromatographed on a Bio-Rad Bio-Sil TSK-250 column using 40% acetonitrile, 0.1% TFA as the mobile phase. A single peak of absorbance at 214 nanometers (nm) elutes from the column in a volume range equivalent to 7,000 to 10,000 daltons. This position is between the two peptide standards, cytochrome C and aprotinin, which are 12,500 daltons and 6,500 daltons, respectively.

The amino acid composition based on a molecular weight of 8,000 was estimated as follows:

| Alanine | 4 | Leucine | 6 |
|---|---|---|---|
| Arginine | 5.5 | Lysine | 7.8 |
| Asparagine or aspartic acid | 5.6 | Methionine | 2.3 |
|  |  | Phenylalanine | 2.6 |
| Cysteine | N/A | Proline | 4 |
| Glutamine or glutamic acid | 8.2 | Serine | 5.6 |
|  |  | Threonine | 2.9 |
| Glycine | 5 | Tryptophan | N/A |
| Histidine | N/A | Tyrosine | 2 |
| Isoleucine | 5 | Valine | 4 |

The partial amino acid sequence from the N-terminus was estimated as follows:

(1) (10)
(Gly)—Leu—Leu—?—Gly—Pro—(Pro)—(Arg)—Lys—Ile—Ile—Lys—

(19) (24)
Ser—Leu—Glu—Asp—Met—Val—Gly—(Asp)—Gln—Pro—Asn—Glu.

In addition to this novel 8,000 dalton peptide, a second fraction (3.5 to 9.5 mL having activity in the DHP binding assay was obtained. Chromatography of this low molecular weight material on Waters μBondapak $C_{18}$, as in Example 1, indicates that this active material elutes in the void volume.

c) Ligand binding assay

Preparation of microsomes and ligand binding was carried out essentially as described previously by Janis et al, supra. Frozen rat hearts (Pel-Freeze) were thawed in 50 mM HEPES buffer (i.e., N-2-hydroxyethylpiperazine-N'-2-ethanesulfonic acid, free acid), pH 7.0, and the atria removed. 5 grams (g) of ventricular myocardium were minced with scissors and homogenized in 50 mL HEPES buffer with a Brinkman Polytron PT20 probe at setting 7 for 10 seconds. This was repeated 2 times with a 10 second cooling on ice between each homogenization. The homogenate was centrifuged at 5,000 ×g for 10 minutes at 4° Centigrade (C). The supernatant fraction was removed and centrifuged at 48,000 ×g for 30 minutes. The resultant microsomal pellet was resuspended in buffer and subsequently used in the assay as described below. Protein was determined by the method of Bradford (Anal. Biochem. 72:248–253, 1976) using bovine serum albumin as standard.

The activity of the fractions isolated by chromatography was defined against a standard curve for competition between the dihydropyridine calcium channel antagonist nimodipine and the calcium channel antagonist, isopropyl 4-(2,1,3-benzoxadiasol-4-yl)-1,4-dihydro-2,6-dimethyl-pyridine-3,5-dicarboxylic acid 1-methyl ester (known as PN 200-110 and referred to hereinafter as [$^3$H]DHP). Said standard curve was derived from data gained by incubating nimodipine and $2 \times 10^{-10}$ M [$^3$H]DHP and microsomal protein per 0.25 mL of assay in 50 mM HEPES buffer (pH 7.0) at 25° C. for 45 minutes and 37° C. for 30 minutes. A cocktail of protease inhibitors ($1 \times 10^{-6}$M aprotinin, $5 \times 10^{-5}$M benzamidine and $5 \times 10^{-5}$M leupeptin) was used but did not inhibit control binding. Said cocktail of protease inhibitors was used to prevent breakdown of the isolated fractions during the assay by proteases which may be present in the membranes or fractions themselves and to exclude the possibility that proteases sensitive to these inhibitors contributed to the activity of the fraction. Following incubation, the bound drug was separated from the free by rapid filtration through Whatman GF/B filters using a Brandel Harvester, followed by two consecutive 1 mL buffer washes at 22° C. The filters were placed in scintillation vials with 5 mL of liquid scintillation fluid. Samples were counted in a Beckman LS 1800 liquid scintillation counter at an efficiency of approximately 55%. Nonspecific binding was defined as the amount of radioligand (i.e., [$^3$H]DHP bound in the presence of nimodipine, which was 10% of total binding. The fractions isolated from stomach were evaluated in the ligand binding assay substantially as described above. Fractions were dissolved in 50 mM HEPES (pH 7.0) and protein concentration was estimated by UV absorption. The pH was carefully monitored and maintained at 7.0 by the addition of 1 M HEPES. All fractions were centrifuged and the supernatants assayed. Binding experiments were performed under sodium vapor light.

d) Results

Ligand Binding

Fractions eluting from the reverse phase column in the approximately 43%–48% acetonitrile range showed activity in the ligand binding assay (16% to 29% inhibition of DHP binding). Re-chromatography of these on the analytical reverse phase column resulted in the active fraction eluting at 47% acetonitrile.

Approximately 23 μg of this protein produced 51% inhibition of [³H]DHP binding. Chromatography of this on Bio-Rad Bio-Sil TSK 250 resulted in the active fraction eluting with an apparent size of 7,000 to 10,000 daltons. Approximately 100 μg of this fraction gave 56% inhibition in the DHP binding assay.

The low molecular weight (active as measured in the ligand binding assay) substance separated from the large peptide was found to have a molecular weight of less than 1,000 daltons.

e) Electrophysiology

In order to further demonstrate that this endogenous calcium channel modulating substance inhibits the $Ca^{2+}$ channel, the following study was undertaken (electrophysiologic methods used were described by Cohen and McCarthy, *J. Physiol.*, 387:195-225, 1987).

Rat anterior pituitary (GH₃) cells were bathed in Tyrode's solution containing NaCl (150 mM), KCl (4.0 mM), CaCl₂ (9.0 mM), MgCl₂ (0.5 mM), dextrose (5 mM) and HEPES (10 mM, pH 7.5). The tip of a patch electrode was filled with a solution containing CsCl (108 mM), tetrabutylammonium chloride (10 mM), BAPTA, i.e., 1,2-bis-(2-aminophenoxy)ethane-N,N,N',N'-tetraacetic acid (11 mM), CaCl₂ (0.9 mM), MgCl₂ (6 mM), adenosine triphosphate (5 mM) and HEPES (20 mM, pH 7.2). This solution is designed to eliminate all potassium channel currents and to slow rundown of the calcium channel currents. After the initial filling of the tip, the patch electrode was back-filled with the above-described solution plus the dissolved endogenous calcium channel modulating substance at a concentration of 1.6 to 5 μg/mL. The patch electrode was then mounted under positive pressure to allow both mixing and diffusion of drug into the tip. A high resistance seal was made to the cell by applying negative pressure and subsequently, the membrane beneath the electrode was disrupted by an increase in negative pressure. Recordings of inward calcium channel currents were performed in a bath solution of tetraethylammonium chloride (117 mM), BaCl₂ (20 mM), MgCl₂ (0.5 mM), tetrodotoxin ($2 \times 10^{-4}$ mM), dextrose (5 mM), sucrose (32 mM) and HEPES (10 mM, pH 7.5).

Time and voltage-dependent block of the slowly inactivating calcium channels by intracellular addition of the endogenous substance of the present invention was obtained in seven experiments using two separate fractions. It is known that GH₃ rat anterior pituitary cells exhibit little or no inactivation for potentials more negative than −20 millivolts (mV). Over this range, where in control studies there is no inactivation, the endogenous calcium channel modulating substance produced potent time and voltage-dependent block of the dihydropyridine sensitive calcium channels. The onset of block at variable prepulse durations to more depolarized potentials produced potent calcium channel block. It was also shown that said substance has no effect on the voltage-dependence of activation or inactivation of the transient calcium channels which are believed to be available for opening in the steady state. These results are graphically represented in FIG. 4.

Figure 4:
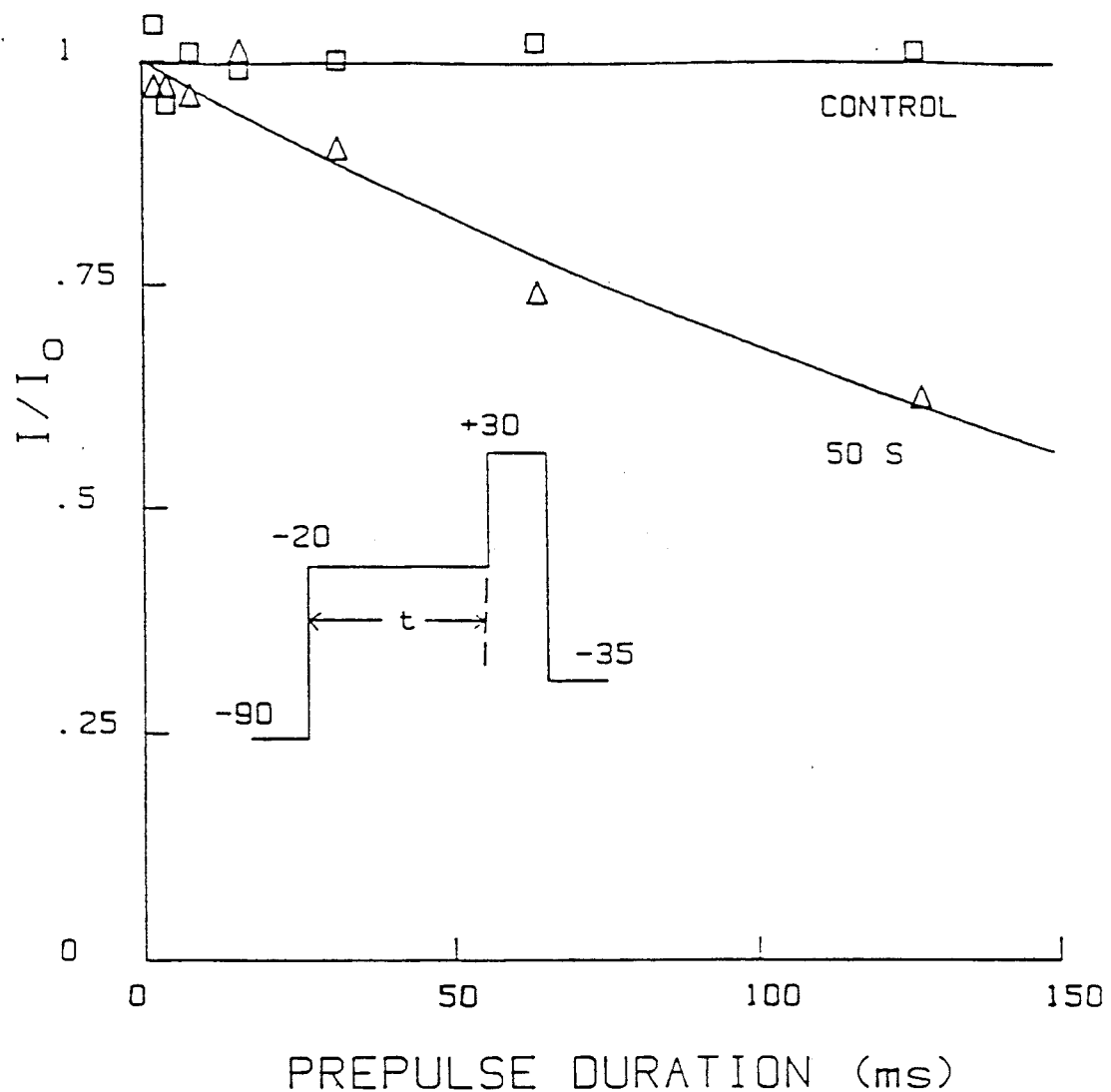
FIG. 4 graphically represents the rate of onset of calcium channel block by the endogenous calcium channel modulating substance of Example 3.
Figure 5:
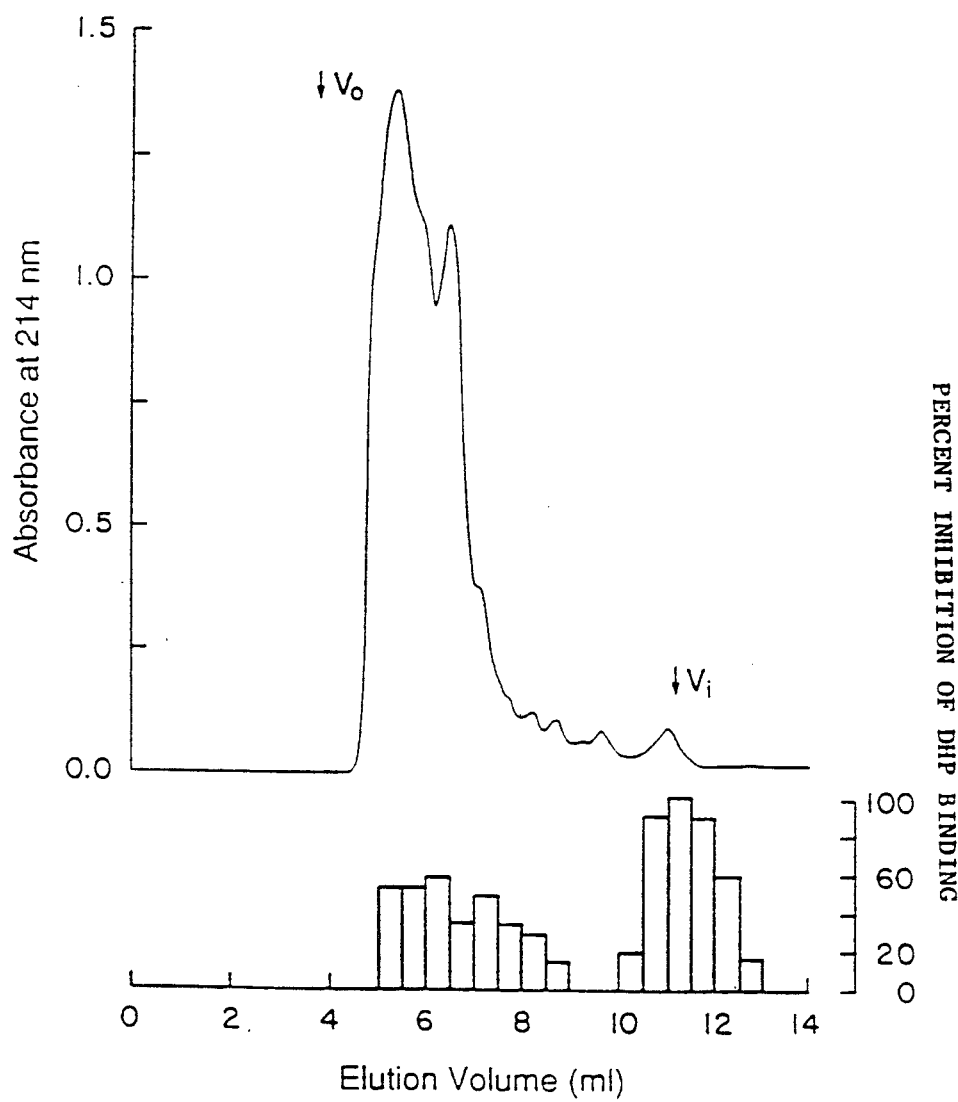
FIG. 5 represents the location of the active fractions isolated from the active fractions obtained from FIG. 1. In this example, the fractions are chromatographed in 40% acetonitrile/0.1% TFA on a Bio-Rad Bio-Sil TSK-250 column. Histogram shows the percent inhibition of DHP binding.
Figure 6:
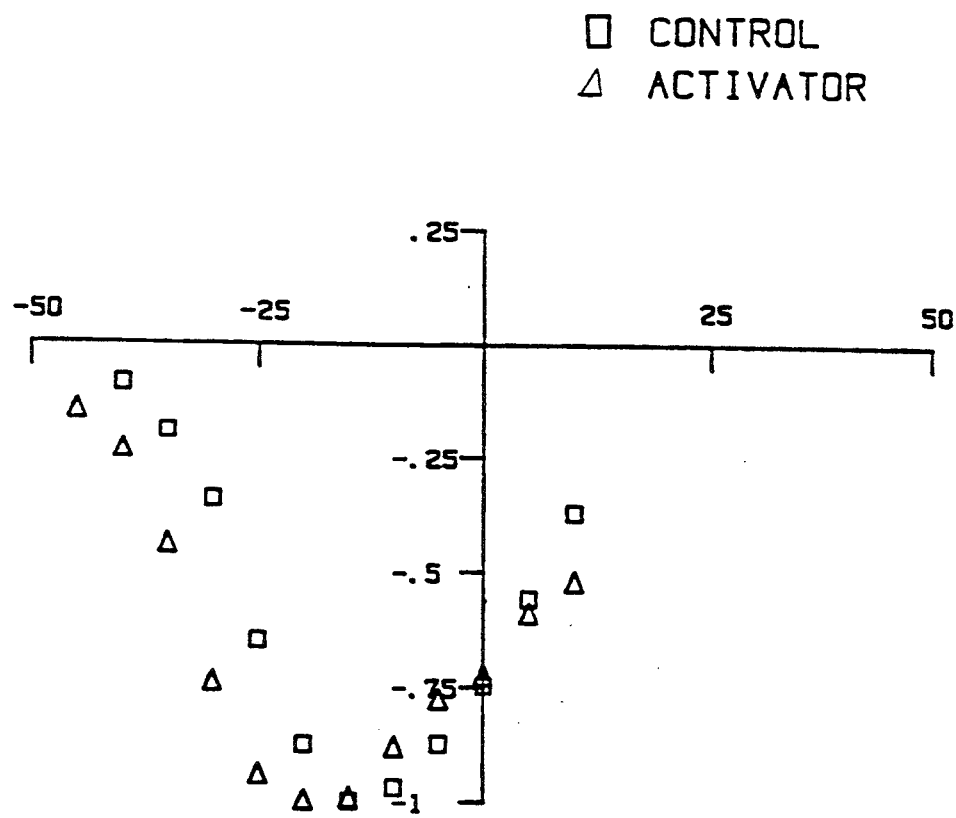
FIG. 6 graphically represents the normalized calcium channel current (abscissa) of $GH_3$ cells at various voltages (ordinate axis) in the absence ($\square$) and presence ($\Delta$) of the activator of Example 5.

FIG. 4 shows the rate of onset of calcium channel block by the endogenous substance of the present invention. The time course of block of the slowly-inactivating channels was determined by tail current analysis as described in Matteson and Armstrong (*J. Gen. Physiol.* 87:161-182, 1986) and Cohen and McCarthy (*J. Physiol.*, 387:195-225, 1987). A protocol was used which takes advantage of the fact that GH₃ cells show little inactivation of inward calcium channel current during prolonged test pulses. For each data point, the membrane potential was held at −90 mV and then stepped to the prepulse potential ($V_p = -20$ mV) for a variable duration prepulse (t). Then a 10 millisecond (ms) test pulse to +30 mV produced maximal activation of the slowly-inactivating Ca channels and tail currents were measured upon repolarization ($V_r = -35$ mV) as shown in the inset of FIG. 4. During the control prepulses (open squares), the fast component of tail current corresponding to the slowly-inactivating channels showed little or no inactivation. The data are fit as a normalized mean of 7 points (342.5 picoamps, pA). With increasing prepulse duration, the endogenous calcium channel modulating substance was added to the pipette (open triangles) and produced time- and voltage-dependent block of the calcium channel. The 7 data points for the substance are fit to the equation:

$$I = (I_o - I_\infty) \exp(-5/\tau \text{onset}) + I_\infty. \text{ For } V_p + -20 \text{ mV}, I_o = 127.05 \text{ pA}, \tau \text{onset} + 0.259 \text{ sec}.$$

The values were normalized by taking the ratio of the fast tail current amplitudes fit by a single exponential (I) to the value obtained by a curve fitting these date points using a non-linear test squares analysis (Colguhoun, Lectures on Biostatistics, Oxford University Press, London) and extrapolating back to time zero ($I_o$). These normalized values ($I/I_o$) were plotted as the ordinate. The cycle length was ten seconds.

The low molecular weight fraction isolated from the crude fraction containing the 8,000 dalton peptide was found to produce time- and voltage-dependent block of the slowly-inactivating channel. The results were essentially the same as shown in FIG. 4 when the less than 1,000 dalton fraction was added to the outside of the GH₃ cells.

EXAMPLE 4

Utilizing the techniques described in the above Examples 1, 2 and 3, endogenous calcium channel modulating substances have also been isolated from calf stomach (abomasum) and blood. The material from calf abomasum (less than 30,000 dalton fraction) was subjected to reverse phase chromatography on a Waters C₁₈ preparative column and eluted at approximately 30% acetonitrile using gradient elution in 0.1% TFA. Size exclusion chromatography resulted in two fractions, the larger of which exhibited characteristics similar to those of the endogenous substance isolated in Example 1. Another active fraction from calf abomasum eluted at 40%-46% acetonitrile and was less than 1,000 daltons in size.

Similarly, the material isolated from blood (a less than 30,000 dalton fraction) was chromatographed on a Waters semi-preparative C₁₈ column, and said material eluted at approximately 38% acetonitrile using gradient elution in 0.1% TFA. When this material was chromatographed on a TSK-250 gel filtration column using 40% acetonitrile in 0.1% TFA as the mobile phase, the activity (as determined in ligand binding assays) eluted in the same volume as a β-lipotropin fragment (amino acids 61-64) which has a molecular weight of 443. The inclusion volume measured by injecting NaCl was more than 10% of an elution range away from this position, indicating this size is reasonably accurate.

EXAMPLE 5

Isolation and Analysis of Endogenous Substances from Hexane Extracts of Calf Brain Extraction 0.5 g of lyophilized calf brain was extracted with 10 volumes of HPLC grade hexane for 10 minutes at room temperature. The extract was centrifuged at 560 ×g for 5 minutes and the resultant supernatant centrifuged at 20,000 ×g. The supernatant is termed the crude hexane extract (CHE).

Chromatography

One mL of the CHE was loaded onto a 1 mL Baker Cyano Solid Phase Extraction (SPE-CN) column equilibrated in hexane. An inhibitory substance was present in the fraction of material that did not bind to the column, i.e. that was unretained. This inhibitor of [$^3$H]DHP binding was retained on an SPE silica column (equilibrated in hexane) and eluted with methanol (but not with (sequential) hexane, CCl$_4$, CHCl$_3$, THF, acetonitrile or isopropanol used before methanol. Fractionation was further accomplished by sequential elution of the SPE CN column with 1 mL of the following solvents: hexane, carbon tetrachloride (CC14), chloroform (CHC13), tetrahydrofuran (THF), acetonitrile and methanol. The presence of an inhibitory activity and a stimulatory activity was detected by ligand binding. These appeared in the CCl$_4$ and CHCl$_3$ fractions, respectively.

HPLC of the CCl$_4$ SPE-CN fraction was performed on a Baker Cyano column (4.6×25 mm). The column was equilibrated in 99% hexane/1% THF and the fraction loaded in the same solvent. The column was eluted with a linear gradient of 1%THF/min in hexane and the activity profile in the in the resultant fractions determined by ligand binding.

Results

Hexane extractable activities from lyophilized calf brain elute from SPE-CN columns with CCl$_4$ (inhibitor) and CHCl$_3$ (stimulator) as detected by ligand binding. Subsequent fractionation of the SPE-CN CCl$_4$ fraction on an analytical HPLC Cyanocolumn shows that the active material elutes with 10%-13%THF under the described conditions. This fraction shows no inhibition of nitrendipine binding to antinitrendipine antibodies. The stimulatory fraction (SPE-CN CHCL$_3$ fraction) was also shown to either increase or decrease calcium currents in the electrophysiological assay.

It is known, however, that the synthetic drug Bay K8644, which also increases calcium channel current in an analogous fashion, can produce inhibition depending on the precise membrane potential and channel state. Therefore, said stimulator can be expected to cause inhibition under certain conditions, in other cell states or in cells containing channels in certain states.

EXAMPLE 6

Isolation and Analysis of Endogenous Substances from Methanol Extracts of Bovine Brain A commercially available hot methanol extract of bovine brain (Sigma Chemical Co., St. Louis, MO; Type VI, Cat. No. B-1877, lot No. 81F-8375) precipitated by cooling was used as the starting material. Two mg were extracted with 1 mL of hexane. The mixture was microfuged (Tomy MC-150 12,000 ×g for 1 min) and 800 µL of the supernatant was loaded onto a Baker SPE cyanopropyl column (Cat. No. 7021-1) that was equilibrated with 100% hexane. The column was eluted sequentially with 1 mL of each of the following: hexane, CCl$_4$, CHCl$_3$, tetrahydrofuran, acetonitrile, methanol and water. Inhibitory activity in the DHP binding assay (cardiac membranes) was found in the CCl$_4$ and methanol fractions. In addition, an activity in the CHCl$_3$ fraction also inhibited the binding of [$^3$H]nitrendipine to antibodies to DHP and produced apparent stimulation of DHP binding to cardiac membranes.

What is claimed is:

1. Endogenous calcium modulating substance characterized in that said substance is obtained from mammalian brain tissue by extracting said tissue with hexane;
    is eluted by carbon tetrachloride on a Baker Cyano Solid Phase extraction column;
    is eluted from an analytical cyanopropyl column, equilibrated in a mixture of hexane and tetrahydrofuran, at about 9% to 10% tetrahydrofuran;
    carbon tetrachloride eluted substance inhibitory activity is detectable by ligand binding;
    shows no inhibition of nitrendipine binding to antinitrindipine antibodies; and
    inhibits the binding of [$^3$H]DHP to cardiac membranes and produces a time-dependent block of inward calcium channel current in GH$_3$ cells.

2. A modulating substance of claim 1 characterized in that the substance is obtained from mammalian brain tissue by extracting with hexane;
    is eluted by chloroform on a Baker Cyano Solid Phase extraction column;
    the chloroform eluted substance shows apparent stimulator activity as detected by ligand binding; and,
    increases or decreases calcium currents in an electrophysiological assay depending on experimental conditions.

3. A modulating substance of claim 1, that:
    is not retained on a Baker Cyano Solid Phase Extraction column but is retained on a SPE Silica column;
    elutes from it with methanol; and
    the substance inhibits the binding of [$^3$H]DHP to cardiac membranes.

* * * * *